(12) United States Patent
Kokaji

(10) Patent No.: US 10,983,114 B2
(45) Date of Patent: Apr. 20, 2021

(54) METHOD FOR THE IN SITU FORMATION OF BIFUNCTIONAL IMMUNOLOGICAL COMPLEXES

(71) Applicant: StemCell Technologies Inc., Vancouver (CA)

(72) Inventor: Andy Isamu Kokaji, Vancouver (CA)

(73) Assignee: STEMCELL Technologies Inc., Vancouver (CA)

( * ) Notice: Subject to any disclaimer, the term of this patent is extended or adjusted under 35 U.S.C. 154(b) by 249 days.

(21) Appl. No.: 15/580,708

(22) PCT Filed: Jun. 3, 2016

(86) PCT No.: PCT/CA2016/050631
§ 371 (c)(1),
(2) Date: Dec. 8, 2017

(87) PCT Pub. No.: WO2016/197238
PCT Pub. Date: Dec. 15, 2016

(65) Prior Publication Data
US 2018/0188245 A1    Jul. 5, 2018

Related U.S. Application Data

(60) Provisional application No. 62/173,600, filed on Jun. 10, 2015.

(51) Int. Cl.
| | | |
|---|---|---|
| C07K 1/22 | (2006.01) | |
| G01N 33/543 | (2006.01) | |
| G01N 33/569 | (2006.01) | |
| G01N 33/80 | (2006.01) | |
| C07K 16/28 | (2006.01) | |
| C07K 16/44 | (2006.01) | |
| C07K 16/00 | (2006.01) | |
| C07K 16/42 | (2006.01) | |

(52) U.S. Cl.
CPC ......... *G01N 33/54326* (2013.01); *C07K 1/22* (2013.01); *C07K 16/00* (2013.01); *C07K 16/283* (2013.01); *C07K 16/2866* (2013.01); *C07K 16/4283* (2013.01); *C07K 16/44* (2013.01); *G01N 33/54313* (2013.01); *G01N 33/56977* (2013.01); *G01N 33/80* (2013.01); *C07K 2317/31* (2013.01); *C07K 2317/32* (2013.01); *C07K 2317/35* (2013.01)

(58) Field of Classification Search
CPC .................................................... C07K 1/22
USPC ...................................................... 424/130.1
See application file for complete search history.

(56) References Cited

U.S. PATENT DOCUMENTS

| | | | |
|---|---|---|---|
| 4,868,109 A | 9/1989 | Lansdorp | |
| 2002/0081635 A1* | 6/2002 | Thomas | C07K 16/28 435/7.21 |

FOREIGN PATENT DOCUMENTS

| | | |
|---|---|---|
| WO | WO 00/73794 A2 | 7/2000 |
| WO | 2014/138887 A1 | 9/2014 |
| WO | 2015/109389 A1 | 7/2015 |

OTHER PUBLICATIONS

The 1988 Stratagene catalog (2 pages).*
Delaive et al (Journal of Immunological Methods, 2008, 334: 51-58).*
Gordon, R. et al., "A simple magnetic separation method for high-yield isolation of pure primary microglia", Journal of Neuroscience Methods, Elsevier Science Publisher B.V., Amsterdam, NL, vol. 194, No. 2, p. 287-296, Jan. 15, 2011.
Kuhara, M. et al., "Magnetic Cell Separation Using Antibody Binding With Protein A Expressed on Bacterial Magnetic Particles", Analytical Chemistry, American Chemical Society, US, vol. 76, No. 21, p. 6207-6213, Nov. 1, 2004.
Zhao et al. Chinese Mater's Theses, Full-Text Database, p. B020-65, Dec. 15, 2008.

* cited by examiner

*Primary Examiner* — Sean E Aeder
(74) *Attorney, Agent, or Firm* — Bereskin & Parr LLP/S.E.N.C.R.L., s.r.l.; Micheline Gravelle

(57) ABSTRACT

An improved method for the preparation of tetrameric antibody complexes directly on the surface of target entities in a sample is described. In particular, this method involves linking, in the sample, a first target entity with a second target entity in a sample using antibodies with specificity for the first and second target entities.

12 Claims, 9 Drawing Sheets

METHOD FOR THE IN SITU FORMATION OF BIFUNCTIONAL IMMUNOLOGICAL COMPLEXES

RELATED APPLICATION

This application is a national phase entry application of Patent Cooperation Treaty Application No. PCT/CA2016/050631, filed Jun. 3, 2016 (which designates the U.S.), which claims the benefit under 35 USC § 119(e) from U.S. Provisional Application No. 62/173,600, filed on Jun. 10, 2015, which is are incorporated herein by reference in its their entirety.

FIELD

The present disclosure relates to methods and kits for preparing tetrameric antibody complexes directly on the surface of target entities in a sample, rather than preparing the bifunctional immunological complexes prior to adding them to the sample.

BACKGROUND

Specific labeling of biological targets such as molecules, DNA, proteins or cells is desired for many different applications in the life science and medical fields. Labeling provides a sensitive way to detect or manipulate the targets from within complex biological samples using the new functional or physical properties of the label (fluorescence, magnetism, density, enzymatic activity, radioactivity, etc.). For example, antibody mediated targeting of any bioactive drug to a biological target can increase its potency and efficacy, while reducing toxicity to surrounding cells and tissue.

The use of antibodies and recombinant proteins has been used to specifically label biological targets for a variety of applications. Most of these approaches are for the identification of the target entity for the purpose of characterization, phenotyping or isolation. The use of antibodies for isolating a biologic entity is considered immunoaffinity purification.

In many applications it is desirable to enrich, or alternatively deplete, certain target entity populations in a biological sample. For example, the separation of specific cell types from peripheral blood, bone marrow, spleen, thymus and fetal liver is key to research in the fields of hematology, immunology and oncology, as well as diagnostics and therapy for certain malignancies and immune disorders. The separation of specific cell types from these heterogeneous samples is key to research in these fields, diagnostics and therapy for certain malignancies and immune/hematopoietic disorders.

Hematopoietic cells and immune cells have been separated on the basis of physical characteristics such as density and on the basis of susceptibility to certain pharmacological agents which kill cycling cells. The advent of monoclonal antibodies against cell surface antigens has greatly expanded the potential to distinguish and separate distinct cell types. There are two basic conceptual approaches to separating cell populations from blood and related cell suspensions using monoclonal antibodies. They differ in whether it is the desired or undesired cells which are distinguished/labeled with the antibody(ies).

In positive selection techniques, the desired cells are labeled with antibodies and removed from the remaining unlabeled/unwanted cells. In negative selection, the unwanted cells are labeled and removed. Antibody/complement treatment and the use of immunotoxins are negative selection techniques, but FACS sorting and most batch-wise immunoadsorption techniques can be adapted to both positive and negative selection.

Tetrameric antibody complexes (TACs) have been extensively used in the development of numerous immunoaffinity cell isolation, positive and negative selection, methods from various tissue types. TACs are immunological complexes of two antibodies of a first animal species, e.g. mouse antibodies, which have been conjugated to form a cyclic tetramer with two monoclonal antibodies of a second animal species, e.g. rat monoclonal antibodies, directed against the Fc-fragment of the antibodies of the first animal species. The process by which TACs are prepared has been described in U.S. Pat. No. 4,868,109 to Peter M. Lansdorp. TACs may be prepared by mixing a first monoclonal antibody which is capable of binding to at least one antigen on the surface of the magnetic particle, and a second monoclonal antibody that binds to the target entity. The first and second monoclonal antibodies are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the F(ab')2 fragments of monoclonal antibodies of a second animal species which are directed against the Fc-fragments of the antibodies of the first animal species. This results in the formation of a mixture of mono-specific and bifunctional TACs, the latter being TACs that contain two different antibodies of the first animal species.

Bifunctional TACs are desired for their ability to crosslink a primary entity, such as an antigen expressed by a given cell, to a secondary entity, such as a magnetic particle. US Patent App No. US2006/0024824 A1 describes a method for separating target entities from non target entities in a sample contained in a vessel without needing to remove the vessel from the magnetic field gradient, and shows examples of how TACs are used with the EasySep™ technology to isolate cells after magnetic labelling. Another potential secondary target could be red blood cells, resulting in the formation of immunorosettes. U.S. Pat. No. 6,448,075 B1 describes a method for separating cells using immunorosettes, which involves contacting a sample with at least one antibody that binds to an antigen on the nucleated cells to be separated linked, either directly or indirectly, to at least one antibody that binds to the erythrocytes (i.e. red blood cells). This results in the formation immunorosettes of the nucleated cells and the erythrocytes to form, which can then be removed from the sample. This method is used in, for example, RosetteSep™ negative selection protocols, where the desired cells are not immunorosetted and therefore remain in the sample once the immunorosettes have been removed.

The presence of mono-specific TACs specific for a given antigen expressed on the surface of a cell can potentially reduce the available epitopes for the functional bifunctional TACs to bind and crosslink the cell to the secondary entity. For this reason, the ratio between the bifunctional complex and both the mono-specific complexes in the reaction product can be influenced by changing the molar ratio of the antibodies of the first animal species used. For example, the antibody ratio can be skewed to be more specific for the second target entity so that although fewer bifunctional TACs and fewer mono-specific TACs against the primary target entity are formed, there is an increase in the proportion of mono-specific TACs against the secondary target entity.

The current state of the art method to preparing TACs is to mix the antibodies in an aqueous buffer. Once formed, the TACs are mixed with primary target entities and subsequently with a secondary target entity. This results in bifunctional TACs to first bind the primary target entity and then crosslink to the secondary target entity. This approach has been extensively used a wide variety of applications, such as EasySep™ and RosetteSep™ technologies.

SUMMARY

The present invention relates to an unexpected and improved method for preparing bifunctional tetrameric antibody complexes (TACs) directly on the surface of a target entity in an aqueous sample, rather than preparing the bifunctional TACs prior to adding them to the sample.

This new approach was unexpected as the current state of the art method only describes the formation of TACs in isolation, prior to the addition of the TACs to the target entities. This novel approach offers several advantages to the state of the art method as (a) it provides the ability to selectively isolate for target entities with high expression of a target antigen, and (b), storing individual antibodies are more stable than TACs and can therefore be stored for longer term at low temperatures or lyophilized.

The current state of the art method to prepare TAC complexes is to mix the antibodies in an aqueous buffer. To preferentially form bifunctional TAC complexes, a molar ratio of 1:1:2 of antibodies against the first target entity, second target entity and crosslinking antibody, respectively, is added. The predicted outcome of the TACs is 25% primary<>primary: 50% primary<>secondary: 25% secondary<>secondary. Once formed, the TAC complexes are then used to label a first target entity or entities. Using this approach labelled target entities are subsequently mixed with a secondary target entity allowing the bifunctional TAC bound to the first target entity to bind to its secondary target entity.

The improved method described herein was not only unexpected but also offered performance improvements. Antibody binding kinetics would suggest that the majority of antibody complexes would form in solution and the formation of bifunctional TAC complexes on the primary target entity would be limited. What was found was that cells were isolated with higher purity using this approach. This approach offers several advantages to the state of the art method as it can selectively isolate for target entities with high expression of a target antigen, and secondly, individual antibodies are more stable than immune complexes due to aggregation and can therefore be stored for longer term.

In one embodiment, a method for linking a first target entity with a second target entity in a sample is disclosed, the method comprising:
  (a) contacting the first target entity with a first antibody that is specific for the first target entity wherein the first antibody binds to the first target entity in the sample;
  (b) adding a second antibody to the sample that binds the second target entity;
  (c) adding a third antibody to the sample that is specific for the first and second antibodies wherein the third antibody binds to said first and second antibodies, thereby forming a tetrameric antibody complex;
  (d) adding the second target entity wherein the second antibody binds to the second target entity, thereby linking the first and second target entity through the tetrameric antibody complex.

The first target entity is preferably biological material that one wishes to separate from a sample such as cells, bacteria, viruses, cell organelles, proteins or nucleic acids.

In one embodiment the first target entity is a cell including, but not limited to, T cells, B cells, NK cells, dendritic cells, monocytes, basophils, mast cells, progenitor cells, stem cells and tumor cells.

The second target entity is preferably an inert material or a cell. In one embodiment, the inert material is selected from a particle or bead. In another embodiment, the cell is an erythrocyte.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

(I) Definitions

Figure 1:
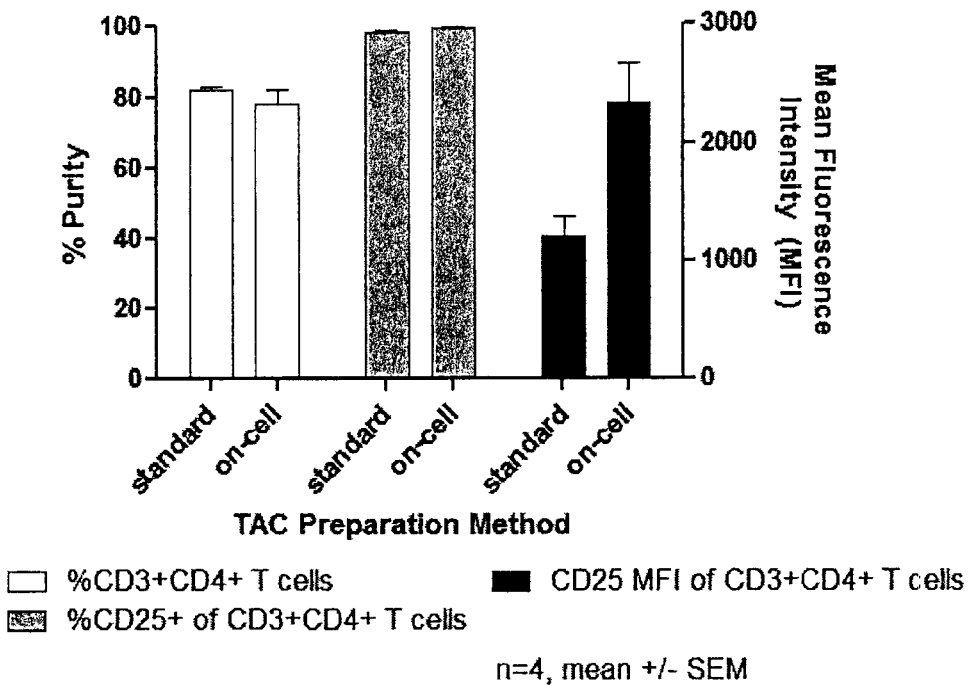
FIG. 1 shows on-cell TAC formation compared to the standard method for EasySep™ Human CD25 Positive Selection.

As used herein, the term "antibody" includes monoclonal antibodies and polyclonal antibodies, antibody fragments (e.g., Fab, and F(ab')2), chimeric antibodies, bifunctional or bispecific antibodies. Antibodies are understood to be reactive against a selected antigen on the surface of a target such as a cell or erythrocyte, if they bind with an appropriate affinity (association constant), e.g. greater than or equal to $10^7$ $M^{-1}$.

As used herein, the term "antibody composition" refers to a composition comprising more than one type of antibody, each antibody binding to a different antigen.

As used herein, the term "antigen" is an entity that can be recognized by an antibody.

As used herein, the term "tetrameric antibody complex" or "TAC" is a complex comprised of two antibodies from a first animal species held in a tetrameric array by two antibodies from a second animal species that binds the two antibodies of the first animal species.

As used herein, the term "target entity" is an entity of interest that will bind to a specific antibody, generally referred to as the "first antibody" herein.

(II) Methods

The present disclosure relates to methods for preparing tetrameric antibody complexes directly on the surface of target entities in a sample, rather than preparing the tetrameric antibody complexes prior to adding them to the sample.

In one embodiment, a method for linking a first target entity with a second target entity in a sample is disclosed, the method comprising:
  (a) contacting the first target entity with a first antibody that is specific for the first target entity wherein the first antibody binds to the first target entity in the sample;
  (b) adding a second antibody to the sample that binds the second target entity;
  (c) adding a third antibody to the sample that is specific for the first and second antibodies wherein the third antibody binds to said first and second antibodies, thereby forming a tetrameric antibody complex;
  (d) adding the second target entity wherein the second antibody binds to the second target entity, thereby linking the first and second target entity through the tetrameric antibody complex.

In one embodiment, the method further comprises:
  (e) separating the first target entity bound to the second target entity from the sample.

The first target entity is any entity that one wishes to target in a sample and is preferably biological material that one wishes to separate from a sample such as cells, bacteria, viruses, cell organelles, proteins or nucleic acids.

In one embodiment the first target entity is a cell including, but not limited to, T cells, B cells, NK cells, dendritic cells, monocytes, basophils, mast cells, progenitor cells, stem cells and tumor cells.

In one aspect of the present invention, the first target entity is a T cell. In another embodiment, the T cell is a $CD25^+$ $CD4^+$ $CD3^+$ cell.

The first antibody is an antibody or fragment thereof that binds to the first target entity. In the case of a cell, the first antibody will bind to an epitope or antigen on the cell. Many cell specific antigens and antibodies thereto are known in the art. One of skill in the art can readily obtain such antibodies or prepare them using techniques known in the art. Examples of cell specific antigens include, but are not limited to, CD2, CD3, CD4, CD8, CD11b, CD11c, CD14, CD15, CD16, CD19, CD20, CD25, CD32, CD34, CD35, CD36, CD43, CD56, CD66b, CD123, CD127, CD138, gamma/delta TCR, SSEA-4, TRA-1-60, HLA-DR, and haptens such as biotin or fluorochromes such as FITC, PE or APC. Antibodies to these antigens are readily available.

Monoclonal antibodies are preferably used in the methods of the disclosure. Monoclonal antibodies specific for selected antigens on the surface of nucleated cells may be readily obtained or generated using conventional techniques that are readily apparent to those of skill in the art.

The disclosure also contemplates aptamers or chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes selected antigens on the surface of differentiated cells or tumor cells.

In one embodiment, the method of the present disclosure is used to separate cells from a sample.

In a positive selection protocol, the desired cells are the target cells. In a positive selection protocol, the first antibody composition will contain at least one antibody specific for the desired cells that one wishes to separate from the sample.

In a negative selection cell separation protocol, the desired cells are not bound by the first antibody and remain in the sample following the removal of the first antibody bound target cells linked to the second target entity. In a negative selection cell separation protocol, the first antibody will be specific for the cells that one wishes to remove from the sample.

In one embodiment, the first antibody is a composition comprising a combination of antibodies specific for different cell types that one wishes to remove from the sample. For example, to prepare a sample enriched in human T cells, one could contact the sample in step (a) with a combination of antibodies that binds to antigens on non-T cells such as CD14, CD16, CD19, CD36, CD56, CD66b, CD123 and Glycophorin A. One of skill in the art can readily determine a suitable combination of antibodies for enriching a particular cell type. In this regard, we refer to Applicant's web site which provides many cell separation kits (www.stemcell.com).

The second target entity is preferably an inert material or a cell. Antibodies or antibody fragments that bind the second target entity can be readily prepared or obtained from available sources.

In one embodiment, the inert material is selected from a particle or bead. In such an embodiment, the second antibody can bind a chemical entity that has been attached to the particle or bead including, but not limited to, proteins, polysaccharides and synthetic polymers. In one embodiment, the particles are coated with polyethylene glycol (PEG) or dextran. In such an embodiment, the second antibody or fragment thereof will bind to the PEG or dextran attached to the particle. In another embodiment, the particles are magnetic. Examples of magnetic particles disclosed in the present application include ferrofluids, other colloidal magnetic particles and particles in suspension.

Figure 7:
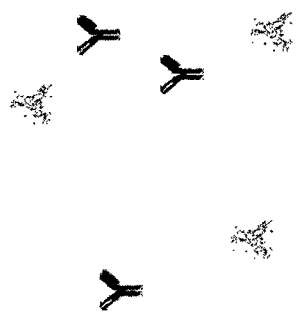
FIG. 7 shows an on-cell TAC formation method and its use for EasySep™ Positive Selection.
Figure 7:
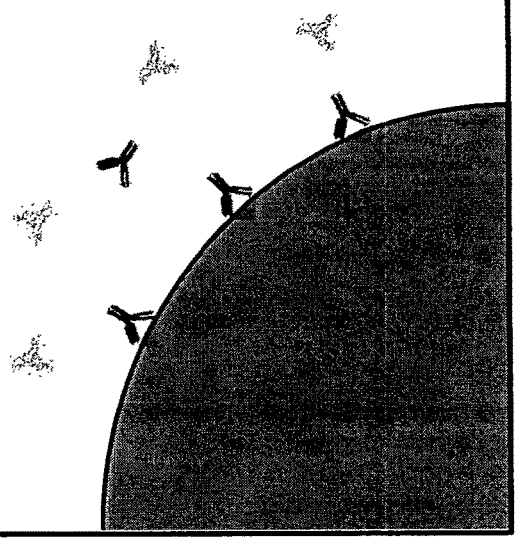
Figure 7:
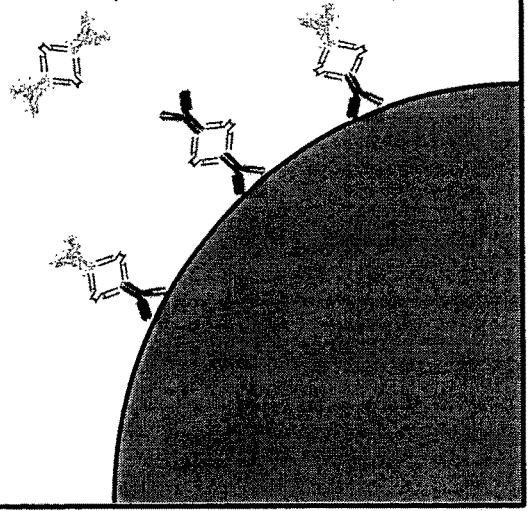
Figure 7:
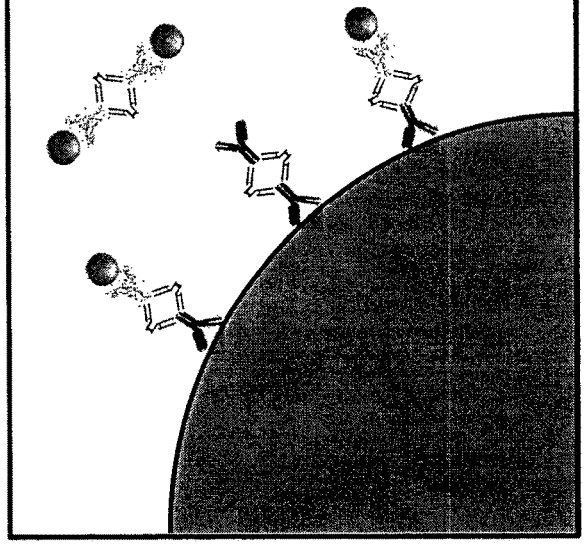
Figure 8:
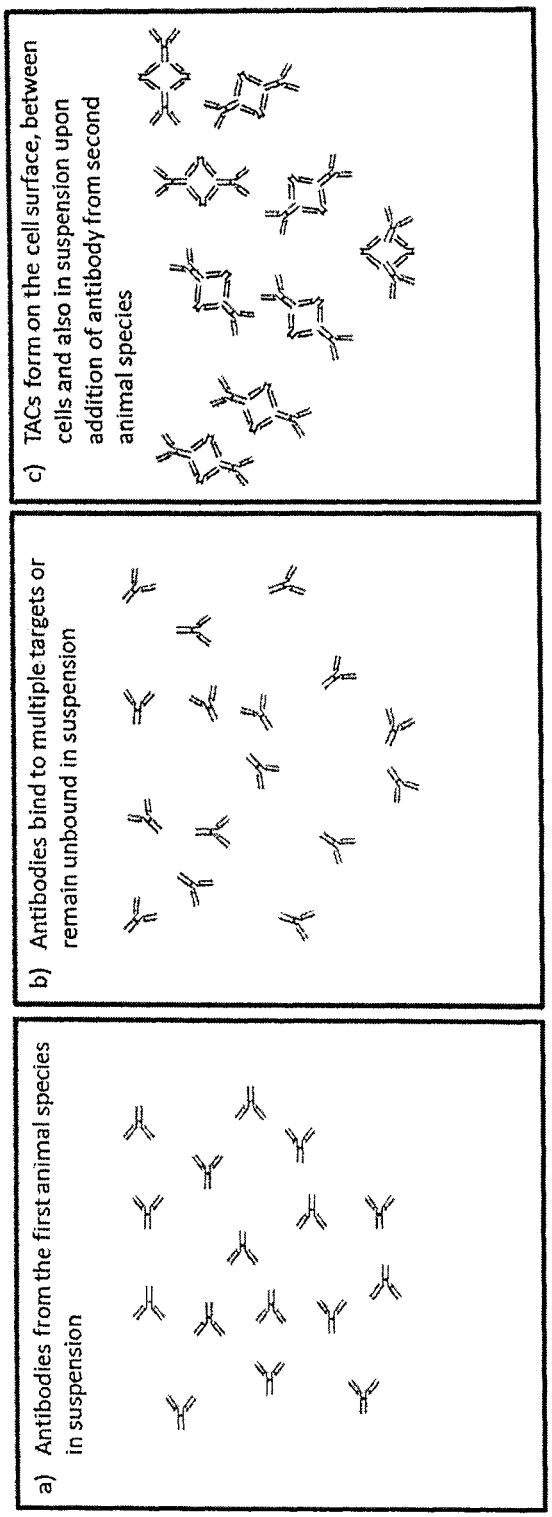
FIG. 8 shows an on-cell TAC formation method and use when multiple target antibodies are used.
Figure 9:
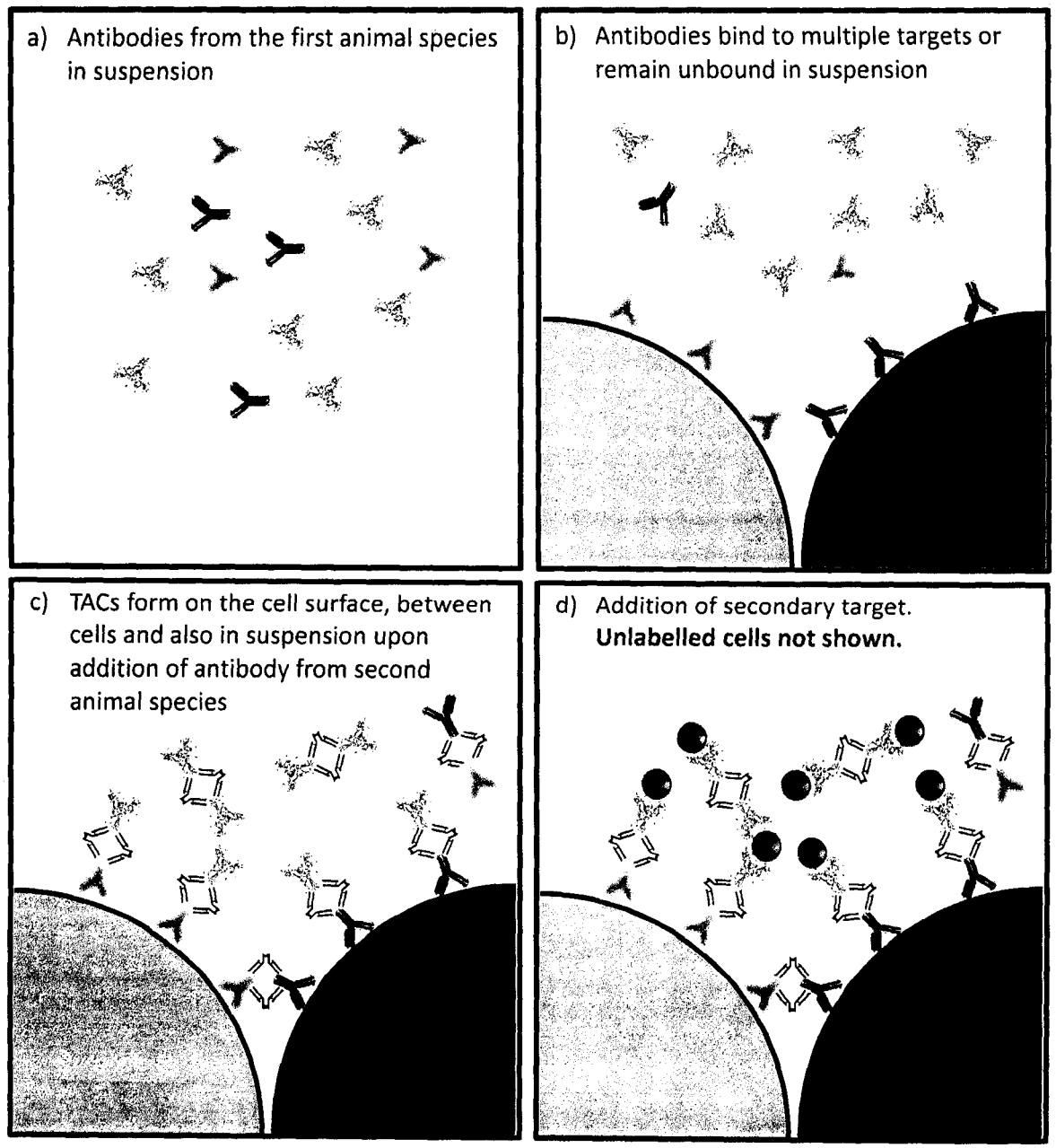
FIG. 9 shows an on-cell TAC formation method and its use for EasySep™ Negative Enrichment.

In such an embodiment, the magnetically labelled target cell is placed in a magnetic field of sufficient strength to separate the magnetically labelled cell from non-magnetically labelled cells. The cells labeled with magnetic particles migrate towards the magnetic field and are held in place allowing the non-magnetic cells to be easily separated from the cells labeled with magnetic particles. Methods to magnetically separate cells are known in the art, for example in US 2006/0024824 A1 which is incorporated herein by reference. This method is also shown schematically in FIG. 7 (positive selection) and FIG. 9 (negative selection).

Figure 10:
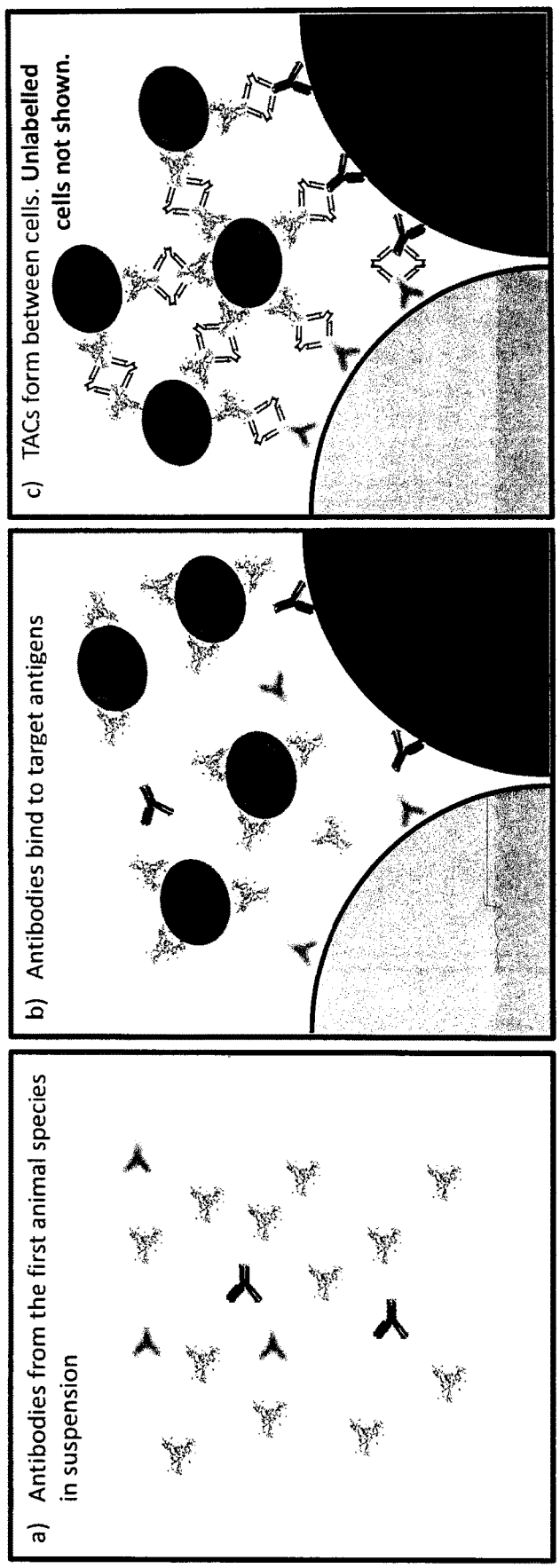
FIG. 10 shows an on-cell TAC formation method and its use for RosetteSep™ Negative Enrichment.

In another embodiment, the first target entity is a cell and the second target entity is an erythrocyte present in the sample such as peripheral blood, buffy coat-treated blood, bone marrow or leukopheresis samples. The second antibody will bind an antigen present on erythrocytes such as glycophorin A. In such an embodiment, cell-erythrocyte conjugates are formed which can be separated from unbound cells. The cell-erythrocyte conjugates (or immunorosettes) may be separated from unbound cells using density gradient centrifugation or by sedimentation. Methods for separating cells using immunorosettes are known in the art, for example, in U.S. Pat. No. 6,448,075, which is incorporated herein by reference. This method is also shown schematically in FIG. 10.

The third antibody is one that can bind the first and second antibody so as to form the tetrametric antibody complex (TAC). In one embodiment, the third antibody or antibody fragment binds to the Fc portion of the first and second antibodies. In such an embodiment, the first and second antibodies are from the same animal species and the third antibody is from a different species. The third antibody is preferably an F(ab')2 fragment of a monoclonal antibody of a second animal species which is directed against the Fc-fragments of the antibodies of the first animal species.

In another embodiment, there are equal numbers of first and second antibodies. In another embodiment, there are unequal numbers of first and second antibodies. In one embodiment, a molar ratio of 1:1:2 of anti-cell, anti-particle and digested F(ab')2 fragment of a crosslinking antibody is added. In another embodiment, the first, second and third antibodies present in a molar ratio of 3:1:4, 2:1:3, 1:2:3 or 1:3:4, respectively.

In one alternate embodiment of the method of the invention, the second antibody can be added at the same time as the first antibody. In yet another embodiment, both the second and third antibodies can be added at the same time as the first antibody, provided they are not mixed together to form a TAC before they are added to the sample. It is an essential feature of the method that the TACs form in situ in the sample.

(III) Kits

The present disclosure also provides a kit for linking a first target entity with a second target entity. As noted previously, the method of the present disclosure requires that the TAC is formed in situ and not prior to adding to the sample. Accordingly, the first, second and third antibodies will not be present in the same container prior to the use.

In one embodiment, the kit comprises:
(a) first container containing a first antibody or antibody composition that binds to the first target entity and a second antibody or antibody composition that binds to the second target entity; and
(b) a second container containing a third antibody that binds to both the first and second antibody or antibody composition.

In another embodiment, the kit comprises:
(a) first container containing a first antibody or antibody composition that binds to the first target entity;
(b) a second container containing a second antibody or antibody composition that binds to the second target entity; and
(c) a third container containing a third antibody that binds to both the first and second antibody or antibody composition.

In yet another embodiment, the kit comprises:
(a) first container containing a first antibody or antibody composition that binds to the first target entity, a second antibody or antibody composition that binds to the second target entity and a non-mouse IgG1 Fc receptor blocking antibody; and
(b) a second container containing a third antibody that binds to both the first and second antibody or antibody composition.

The kit will preferably include instructions for the methods of using the kit including the methods disclosed herein.

The kit is preferably used to separate cells from a sample using the methods disclosed herein.

The kit may also include the second target entity such as a particle or bead.

The first, second and third antibodies (or antibody compositions) are as defined in Section (II)—Methods.

The first and second container can be any container that is useful for containing antibodies such as a vial or a blood collection tube. The antibodies may be lyophilized.

The following non-limiting examples are illustrative of the present invention.

EXAMPLES

Example 1

EasySep™ Immunomagnetic Positive Selection Using On-Cell TAC Formation

Human regulatory T cells (Tregs) were initially characterized as CD3+ CD4+ T cells that express high levels of cell surface CD25 (Human CD25+ CD4+ T regulatory T cells suppress nave and memory T cell proliferation and can be expanded in vitro without loss of function. (2001). M K Levings, R Sangregorio, M G Roncarolo. The Journal of Experimental Medicine 193: 11, 1295-1302). In order to purify Tregs, cells expressing high levels of CD25 must be isolated from a heterogeneous population of cells in peripheral blood. Immunomagnetic cell isolation requires the use of antibodies of varying affinity for their given target antigen and a method to link a superparamagnetic particle to the specific antibody. EasySep™ cell isolation technology using TACs and magnetic particles can be used to label and positively select human CD25+ cells from a heterogeneous mixture of peripheral blood mononuclear cells (PBMCs). A proportion of PBMCs expressing high levels of cell surface CD25 can be identified as Tregs using the intracellular transcription factor FOXP3; whereas, cells expressing intermediate levels of cell surface CD25 can be a mixture of non-Tregs such as memory or recently activated T cells that do not express FOXP3.

In order to isolate Tregs from PBMCs, EasySep™ immunomagnetic positive cell isolation using either TACs prepared in the standard method prior to addition to a cell suspension containing a target cell population or the method described in this disclosure of forming bifunctional TACs on the surface of a target cell population.

Human PBMC were prepared from either Ficoll® density gradient separation of whole human blood or from leukopheresis samples washed with PBS+2% fetal bovine serum (FBS)+1 mM ethylenediaminetetraacetic acid (EDTA). PBMCs were resuspended at $1\times10^8$ cells/mL in PBS+2% FBS+1 mM EDTA.

TACs specific for human CD25 and PEG were prepared using the current state of the art method of combining a 1:1:2 molar ratio of anti-human CD25 (mouse IgG1, 10 ug/mL), anti-PEG (mouse IgG1, 10 ug/mL)) and F(ab')2 anti-mouse IgG1 (rat IgG1, 13.6 ug/mL) and anti-human CD32 (mouse IgG2a, 20 ug/mL) in phosphate buffered saline (PBS), pH 7.4. The antibody mixture is incubated for at least 30 minutes, preferably 16-24 hours at 37° C. and stored at 2-8° C. until use as described in U.S. Pat. No. 4,868,109 to Peter M. Lansdorp. For the on-cell TAC approach, two separate antibody cocktails were prepared. Cocktail component A was prepared with anti-human CD25 (10 ug/mL), anti-PEG (10 ug/mL) and anti-human CD32 (20 ug/mL) in PBS pH7.4. Cocktail component B was prepared with 13.6 ug/mL of F(ab')2 anti-mouse IgG1 in PBS pH7.4. The two antibody cocktails were prepared separately and stored at 2-8° C. until use.

For the standard TAC cell labelled method, pre-formed anti-CD25 TACs were added to $1\times10^8$ PBMC/mL suspension for 5 minutes at RT to allow the binding of the pre-formed TAC to the cell surface target. Final concentration of antibodies in the preformed TAC was 0.5 ug/mL anti-CD25, 0.5 ug/mL anti-PEG, 0.68 ug/mL F(ab')2 anti-mouse IgG1. The final concentration of anti-CD32 antibody was 1 ug/mL. The anti-CD32 antibody blocks Fc receptor mediated binding of antibodies to cells expressing CD32.

For the on-cell TAC cell labelling method, the cocktail component A final concentration of 0.5 ug/mL anti-CD25 (cl: M-A251), 0.5 ug/mL anti-PEG (cl: 3F12-1) and 1 ug/mL anti-CD32 (cl: IV3) was added to $1\times10^8$ PBMC/mL suspension for 5 minutes at RT to allow for the binding of the anti-CD25 mAb to the cell surface target. The anti-PEG antibody remains unbound in suspension. Following the 5 minute incubation, a final concentration of 0.68 ug/mL of F(ab')2 anti-mouse IgG1 mAb (cl: P9) is added and incubated for 5 minutes at RT.

The subsequent steps in the EasySep™ cell isolation procedure were identical following the TAC labelling step. Following either the addition of the standard TAC or the on-cell TAC formation protocol, EasySep™ Releasable RapidSpheres™—50200 were added at 50 uL/mL and incubated for 5 minutes. Following the incubation, the sample was diluted with PBS+2% FBS+1 mM EDTA and placed into an EasySep™ magnet for 5 minutes. Following the magnetic incubation, the unlabelled fraction was poured off into a new tube. The positively selected sample in the tube in the magnet was resuspended in PBS+2% FBS+1 mM EDTA and three additional 5 minute magnetic washes were performed. Following their isolation, cells were harvested and analyzed by flow cytometry using antibodies against CD3, CD4 and CD25.

Results

The formation of TACs using the on-cell method was able to isolate cells expressing ~2-fold higher levels of CD25 (CD25 MFI=2339+/−332) compared to the standard method of TACs (CD25 MFI=1217+/−161) when the same concentration of antibodies were used for the formation of the TAC (FIG. 1). Of interest was that the purity of CD3+CD4+ T cells (81.9%+/−1.2% and 77.8%+/−4.0% for the standard and on-cell, respectively) and total CD25+ cells was equivalent (98.0%+/−0.6% and 99.0%+/−0.4% for the standard and on-cell, respectively). The only difference was that the on-cell TAC formation method facilitated the isolation of cells expressing higher levels of CD25 as assessed by the mean fluorescence intensity of fluorochrome conjugated antibody staining assessed by flow cytometry.

Subsequent to the positive selection of CD25+ cells using either the standard or on-cell TAC formation method, the magnetic particles were released from the isolated cells using EasySep™ Release Buffer as described in US patent application WO2014029012 A1. Magnetic particle free cells were subsequently depleted of non-CD4+ T cells using an EasySep™ Human CD4+ T cell negative selection kit. Following the depletion of non-CD4+ T cells, cells were assessed for Treg purity by flow cytometry by staining for CD4, CD25 and intracellular FOXP3 which is a transcription factor specifically expressed by Tregs and its expression linearly correlates with CD25 expression.

Figure 2:
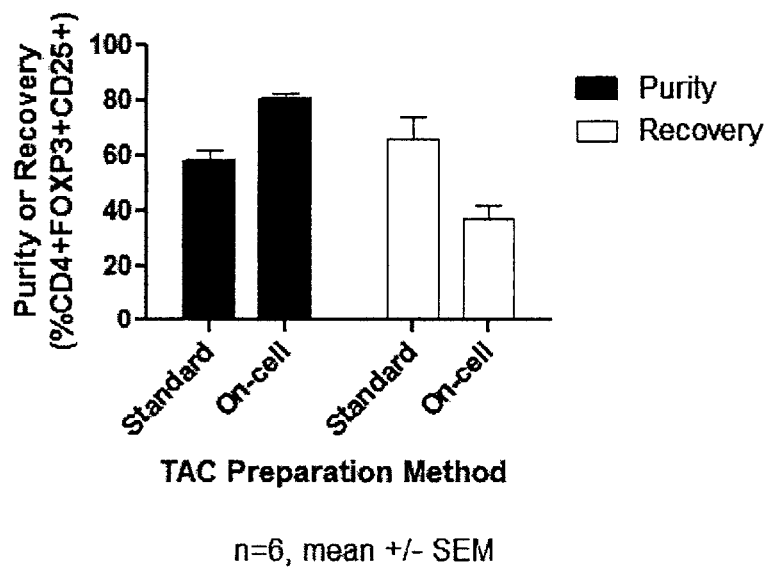
FIG. 2 shows on-cell TAC formation compared to the standard method for EasySep™ Human CD25 Positive Selection followed by particle release and EasySep™ CD4+ T cell negative enrichment.

Cells isolated using the on-cell CD25 TAC formation method resulted in higher final Treg purity (80.9%+/−2.0%) as assessed by CD4, CD25 and FOXP3, compared to the standard method of preparing TACs (58.2%+/−3.8%) (FIG. 2). The only difference between these two isolation methods was the CD25 TAC formation and cell labeling method which resulted in an unexpected and surprising increase in final Treg purity. The recovery of Tregs using the standard method was higher (66.2%+/−7.8%) compared to the on-cell TAC method (37.4%+/−4.8%) which is to be expected due to the higher purity of the isolated cell population.

Taken together, this is a demonstration that on-cell TAC formation can provide an advantage over existing pre-formed TACs for isolation of human regulatory T cells that express high levels of CD25. This approach could be utilized to improve specificity for differential expression levels of target antigens.

Example 2

EasySep™ Immunomagnetic Negative Selection Using On-Cell TAC Formation

In EasySep™ positive selection, the desired cells are labeled with a single TAC specific for a given cell surface antigen and separated from the remaining unlabeled/unwanted cells. In negative selection, the multiple different types of unwanted cells are labeled and removed which requires a more complex mixture of TACs specific for multiple cell surface antigens. Proof of principle experiments were performed to demonstrate the utility of the on-cell TAC formation that it can be used to label multiple target cells in a heterogeneous mixture of cells for Easy-Sep™ immunomagnetic negative selection.

In this example, human PBMC were prepared from either Ficoll® density gradient separation of whole human blood or from apheresis samples washed with PBS+2% FBS+1 mM EDTA. PBMCs were resuspended at $5\times10^7$ cells/mL in PBS+2% FBS+1 mM EDTA. Similar to the on-cell TAC approach for positive selection, two separate antibody cocktails were prepared. Cocktail component A was prepared with antibodies against a combination of cell surface markers depending on the desired cell population including; CD2, CD3, CD4, CD8, CD14, CD16, CD19, CD36, CD43, CD56, CD66b, CD123, gamma/delta TCR, HLA-DR, glycophorin A and antibodies against dextran that recognizes the Easy-Sep™ Dextran RapidSpheres™—50103. Component B was prepared with F(ab')2 anti-mouse IgG1 at an equal molar concentration to the total antibody content in cocktail A. The two antibody cocktails were prepared separately and stored at 2-8° C. until use.

The cocktail component A was added to $5\times10^7$ PBMC/mL suspension and incubated for 5 minutes at RT to allow for binding of the antibodies to their given target antigen. The final concentration of each antibody in cocktail component A against a cell surface marker varied between 0.5-4.0 ug/mL. The anti-dextran antibody specific for the secondary target entity, EasySep™ Dextran RapidSpheres™—50103 remain unbound in suspension. Following the 5 minute incubation, an equimolar concentration of F(ab')2 anti-mouse IgG1 mAb (cl: P9) is added and incubated for 5 minutes at RT. Following the 5 minute incubation, the TAC labelled sample was topped up with PBS+2% FBS+1 mM EDTA and immediately placed into the EasySep™ magnet for 3 minutes. Following the magnetic incubation, the unlabelled desired fraction was poured off into a new tube. The enriched cell populations were harvested and analyzed by flow cytometry using antibodies against CD45, CD3 and CD4, CD19 or CD56.

Results

Figure 3:
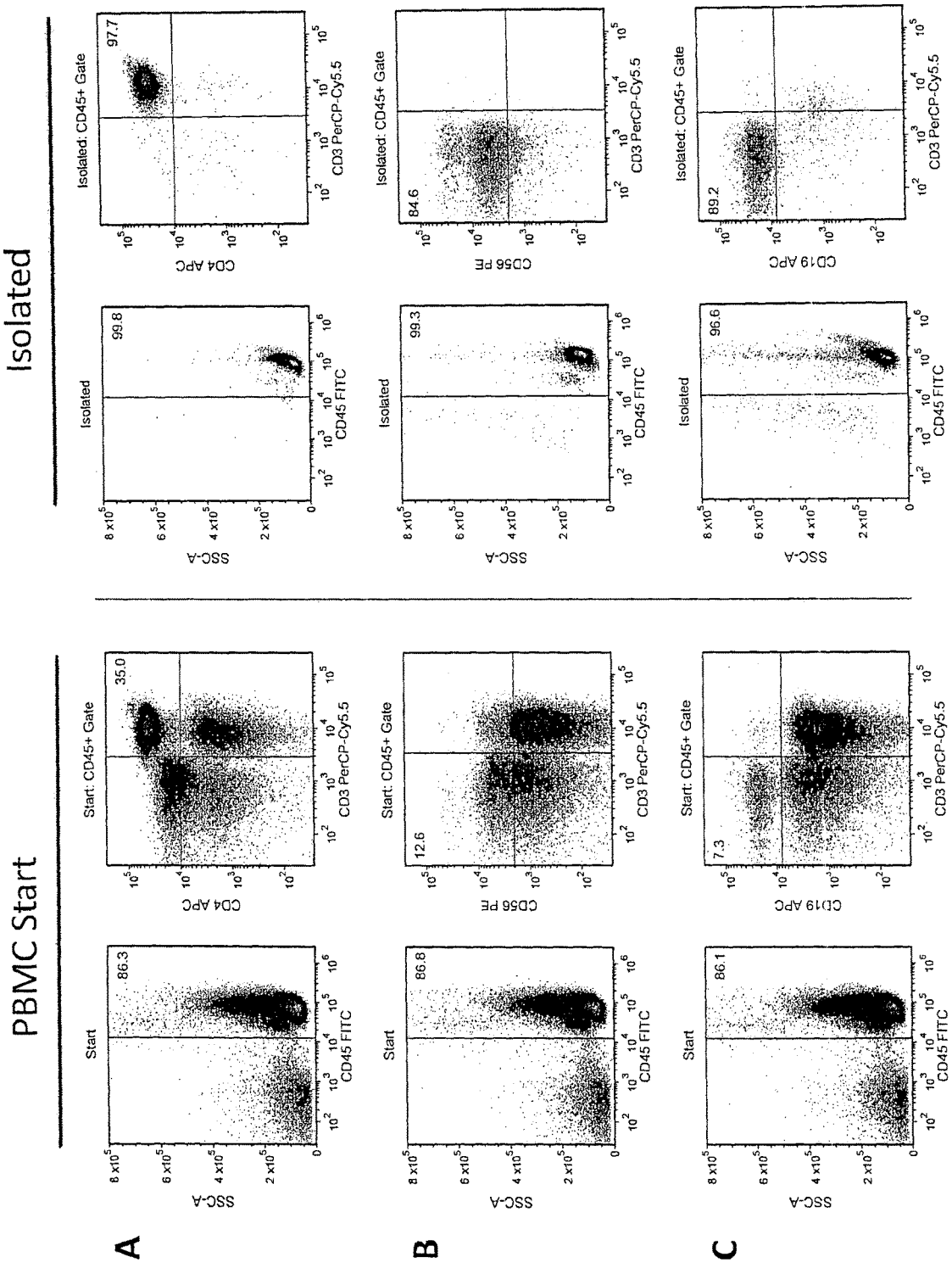
FIG. 3 shows on-cell TAC formation for EasySep™ Negative Enrichment from PBMCs.

Three different antibody cocktails were prepared for the negative enrichment of human CD3+ CD4+ T cells, CD3− CD19+ B cells and CD3− CD56+ natural killer (NK) cells. Each cocktail was composed of antibodies that target undesired cell populations. Using this approach and targeting multiple cell surface target antigens, the on-cell TAC formation method unexpectedly resulted in enrichment of the desired population to a high purity, equivalent to what is typically seen using traditional pre-formed TAC based methods. Starting from a PBMC sample containing 35.0% CD3+ CD4+ T cells gated on CD45+ cells, 97.7% purity of CD3+ CD4+ T cells can be obtained using the on-cell TAC based negative selection approach, with a desired cell recovery of 39.7% (FIG. 3A). Starting with a PBMC sample containing 12.6% CD3− CD56+ NK cells gated on CD45+ cells, 84.6% purity of CD3− CD56+ NK cells can be obtained using the on-cell TAC based negative selection approach, with a desired cell recovery of 34.8% (FIG. 3B). Starting with a PBMC sample containing 7.3% CD3− CD19+ B cells gated on CD45+ cells, 89.2% purity of CD3− CD19+ NK cells can be obtained using the on-cell TAC based negative selection approach, with a desired cell recovery of 21.1% (FIG. 3C). Together these results demonstrate that with a starting cell frequency ranging from 7.3-35.0%, efficient enrichment of a unlabelled lymphocyte populations can be enriched from a heterogeneous mixture of cells using the on-cell TAC labelling procedure that target multiple different cell types simultaneously.

Example 3

RosetteSep™ Immunodensity Negative Selection Using On-Cell TAC Formation

Examples thus far have demonstrated the utility of on-cell TAC formation in EasySep™ immunomagnetic cell separation both in positive and negative selection approaches. In the aforementioned examples, bifunctional TACs are formed on the primary target entity, such as an antigen expressed by a given cell in the absence of the secondary entity, such as an EasySep™ magnetic particle.

Another potential secondary target could be red blood cells present in whole blood. U.S. Pat. No. 6,448,075 B1 describes a method for separating cells using immunorosettes, which involves contacting a sample with at least one antibody that binds to an antigen on the nucleated cells to be separated linked, either directly or indirectly, to at least one antibody that binds to the erythrocytes (i.e. red blood cells). This results in the formation immunorosettes of the nucleated cells and the erythrocytes to form, which can then be removed from the sample when layered over a density gradient medium such as Ficoll. This method is used in, for example, RosetteSep™ negative selection protocols, where the desired cells are not immunorosetted and therefore remain in the sample once the immunorosettes have been removed. RosetteSep™ is a cell labelling and isolation method that uses TACs that crosslink unwanted cells to red blood cells present in whole blood. In this example, both the primary and secondary target entities are present in the same starting sample.

As a proof of principle, the on-cell TAC formation procedure was compared to pre-forming TACs prior to the addition to a whole blood sample containing both the primary and secondary target entities. Similar to the on-cell TAC approach for EasySep negative selection in example 2, a separate antibody cocktail was prepared. Cocktail component A was prepared with antibodies against a combination of cell surface markers specific for non-CD3+CD4+ T cells that included antibodies specific for CD8, CD16, CD19, CD36, CD56, CD66b and glycophorin A. Component B was prepared with anti-mouse IgG1 at an equal molar concentration to the total antibody content in cocktail A. The two antibody cocktails were prepared separately and stored at 2-8° C. until use.

The cocktail component A was added to a whole blood suspension and incubated for 5 minutes at RT to allow for binding of the antibodies to their given target antigen. The final concentration of each antibody in cocktail component A against a cell surface marker varied between 0.5-21.0 ug/mL. Unlike the previous examples, all of the antibodies in cocktail component A can bind to their respective target antigens in the sample. Following the 5 minute incubation, an equimolar concentration of anti-mouse IgG1 mAb (cl: P9) is added and incubated for 5 minutes at RT. Following the 5 minute incubation, the TAC labelled whole blood sample was topped up with PBS+2% FBS and layered over a Ficoll® density gradient and centrifuged. Following the centrifugation step, the cells retained at the interface between the aqueous phase and the Ficoll® density medium was harvested and analyzed by flow cytometry using antibodies against CD45, CD3, and CD4.

Results

Figure 4:
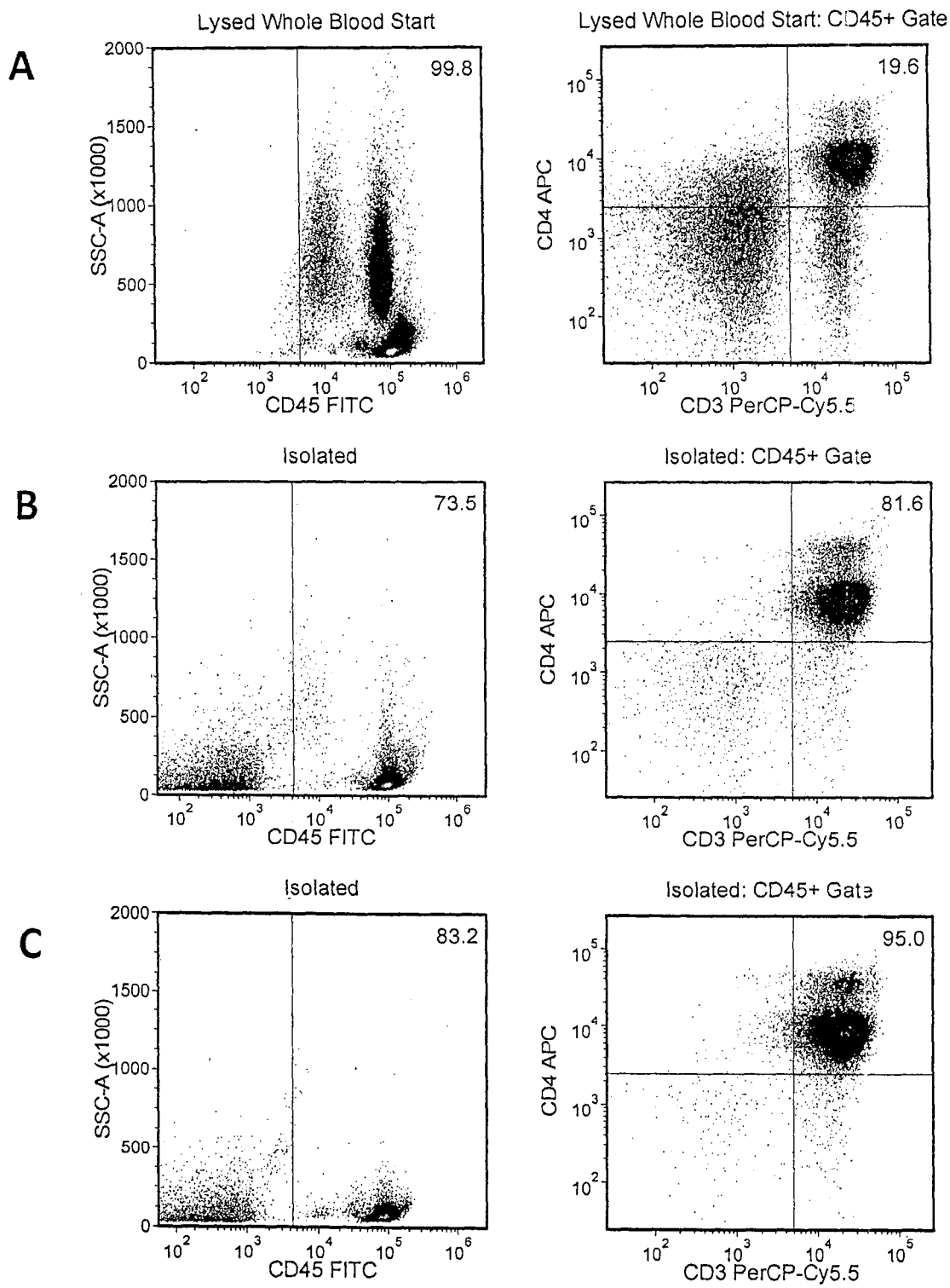
FIG. 4 shows on-cell TAC formation for RosetteSep™ Negative Enrichment from Whole Blood.
Figure 5:
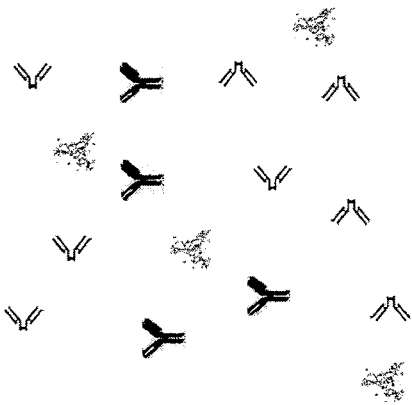
FIG. 5 shows standard TAC compositions and method of use.
Figure 5:
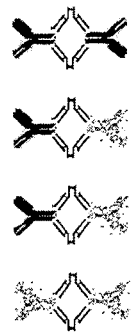
Figure 5:
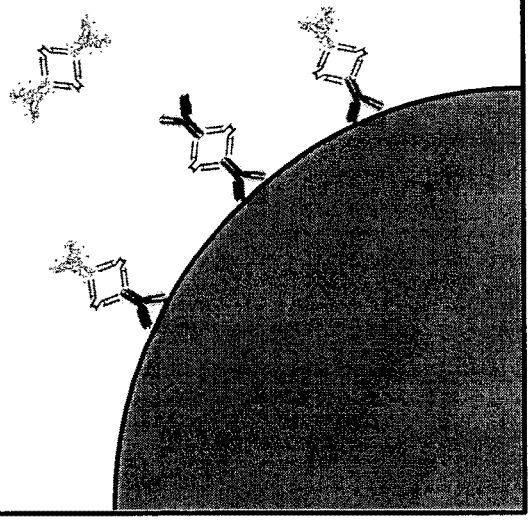
Figure 5:
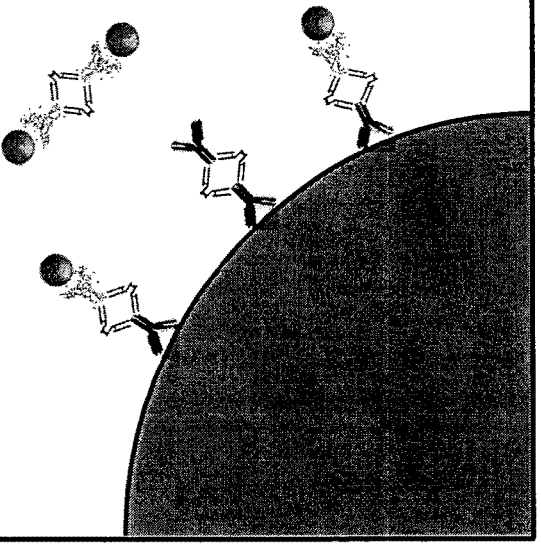
Figure 6:
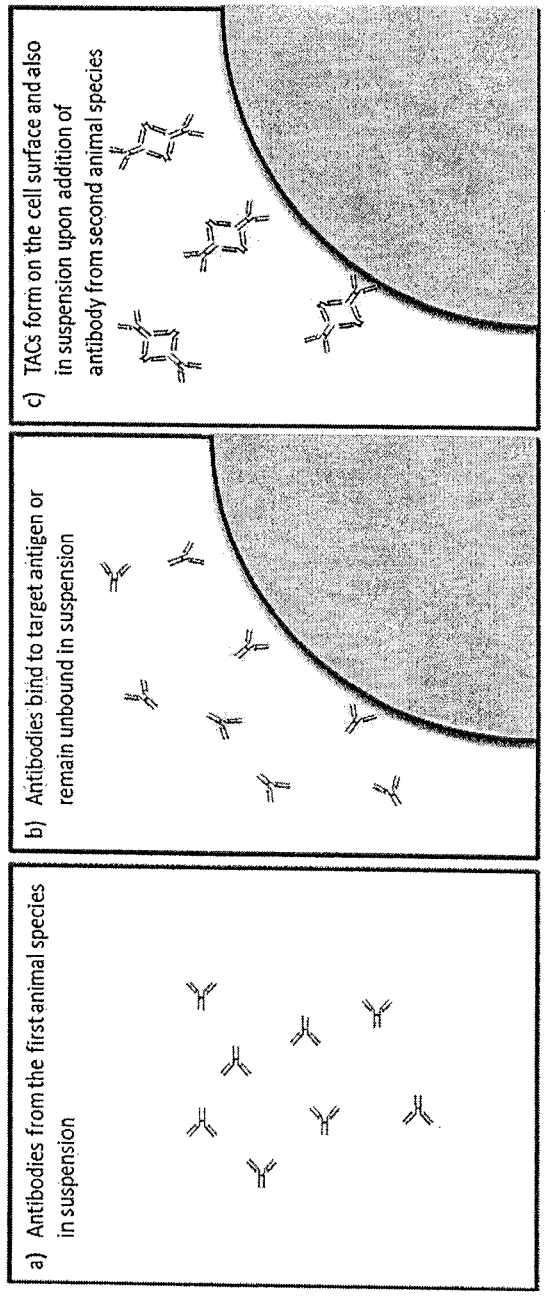
FIG. 6 shows an on-cell TAC formation method.

Using this approach and targeting multiple cell surface target antigens including the primary and secondary target entities, the on-cell TAC formation method unexpectedly resulted in the formation of immunorosettes and the subsequent enrichment of the desired population from 19.6% in the starting red blood cell lysed whole blood starting sample (FIG. 4A) to 81.6% purity of CD45+CD3+CD4+ T cells in the enriched sample, with a desired cell recovery of 24.3% (FIG. 4B). This equates to a 4.2 fold increase in purity compared to the starting whole blood sample. In comparison, the pre-formed TAC resulted in a final purity of 95% of CD45+CD3+CD4+ T cells, with a desired cell recovery of 38.3% (FIG. 4C). As a proof of principle, these results demonstrate that the on-cell TAC formation method can form TACs that can crosslink antibody targeted nucleated cells and red blood cells together to form immunorosettes, however further optimization will be required when both the primary and secondary target entities are present in the starting sample.

While the present disclosure has been described with reference to what are presently considered to be the preferred examples, it is to be understood that the invention is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A method for linking a first target entity with a second target entity in an aqueous sample consisting essentially of:
   (a) contacting the first target entity with a first antibody that is specific for the first target entity wherein the first antibody binds to the first target entity in the sample;
   (b) adding a second antibody to the sample that binds the second target entity;
   (c) adding a third antibody to the sample that is specific for the first and second antibodies wherein the third antibody binds to said first and second antibodies, thereby forming a tetrameric antibody complex;

(d) adding the second target entity wherein the second antibody binds to the second target entity, thereby linking the first and second target entity through the tetrameric antibody complex, wherein the first and/or second antibodies are not mixed together with the third antibody to form the tetrameric antibody complex before they are added to the sample.

2. The method according to claim 1, wherein the third antibody binds to the Fc portion of the first and second antibodies.

3. The method according to claim 1, wherein the first target entity is selected from the group consisting of cells, bacteria, viruses, cell organelles, proteins and nucleic acids.

4. The method according to claim 3 wherein the first target entity is a cell.

5. The method according to claim 4, wherein the first antibody is in a first antibody composition comprising antibodies specific for one or more antigens on the target cell(s).

6. The method according to claim 5, wherein the first antibody composition comprises antibodies specific for one or more antigens selected from the group consisting of CD2, CD3, CD4, CD8, CD14, CD15, CD16, CD19, CD20, CD25, CD32, CD33, CD34, CD35, CD36, CD43, CD45, CD56, CD61, CD66b, CD123, CD127, CD138, alpha/beta TCR, gamma/delta TCR, and HLA-DR.

7. The method according to claim 4, wherein the first target entity is a T cell.

8. The method according to claim 1, wherein the second antibody binds to a particle or a bead.

9. The method according to claim 8 wherein the second antibody binds to PEG or dextran on the particle or bead.

10. The method according to claim 8, wherein the particles are magnetic to form a magnetically labelled tetrameric antibody complex.

11. The method according to claim 10, wherein the magnetically labelled tetrameric antibody complex first target entity is placed in a magnetic field of sufficient strength to separate the magnetically labelled tetrameric antibody complex first target entity from non-magnetically labelled tetrameric antibody complex first target entities.

12. A method for linking a first target entity with a second target entity in an aqueous sample consisting essentially of:

(a) contacting the first target entity with a first antibody that is specific for the first target entity wherein the first antibody binds to the first target entity in the sample;

(b) adding a second antibody to the sample that binds the second target entity;

(c) adding a third antibody to the sample that is specific for the first and second antibodies wherein the third antibody binds to said first and second antibodies, thereby forming a tetrameric antibody complex;

(d) adding the second target entity wherein the second antibody binds to the second target entity, thereby linking the first and second target entity through the tetrameric antibody complex, wherein the first and/or second antibodies are not mixed together with the third antibody to form the tetrameric antibody complex before they are added to the sample;

(e) removing the first target entity linked to the second target entity from the sample.

* * * * *